United States Patent [19]
Hu

[11] Patent Number: 6,037,357
[45] Date of Patent: Mar. 14, 2000

[54] N-BENZOYL-α-ALKYLATED AZATYROSINES AS ANTICANCER AGENTS

[75] Inventor: Ming-Kuan Hu, Taipei, Taiwan

[73] Assignee: Unitech Pharmaceuticals, Inc., Ann Arbor, Mich.

[21] Appl. No.: 09/296,445

[22] Filed: Apr. 21, 1999

[51] Int. Cl.[7] .......................... A61K 31/44; C07D 213/65
[52] U.S. Cl. ............................................. 514/351; 546/300
[58] Field of Search ..................... 514/351, 44; 546/300; 536/24.5, 23.1

[56] References Cited

U.S. PATENT DOCUMENTS 5,869,507   2/1999   Wang et al. ............................ 514/351

OTHER PUBLICATIONS

Junko Fujita–Yoshigaki et al., Azatyrosine inhibits neurite outgrowth of PC12 cells induced by oncogenic Ras, *Oncogene* (1992) 7, 2019–2024.

Shigeharu Inouye et al., L–β–(5–Hydroxy–2–pyridyl)–alanine and L–β–(3–Hydroxyureido)–alanine from Streptomyces, *Chem. Pharm. Bull.* 23(11) 2669–2677 (1975).

W. J. Krzyzosiak et al., Isolation of genes specifically expressed in flat revertant cells derived from activated ras–transformed NIH 3T3 cells by treatment with azatyrozine, *Proc. Natl. Acad. Sci U.S.A..* 89, 4879–4883, Jun. 1992.

Nobuko Shindo–Okada et al., Permanent Conversion of Mouse and Human Cells Transformed by Activated ras or raf Genes to Apparently Normal Cells by Treatment With the Antibiotic Azatyrosine, *Molecular Carcinogenesis* 2:159–167 (1989).

*Primary Examiner*—George C. Elliott
*Assistant Examiner*—Janet Epps
*Attorney, Agent, or Firm*—Brinks, Hofer, Gilson & Lione

[57] ABSTRACT

A series of N-benzoyl-α-alkylated azatyrosines has been synthesized and disclosed. Their in-vitro activities were positive against several human cancer cell lines and significantly more effective than L-azatyrosine. These azatyrosine derivatives were claimed to be new and be useful as anticancer agents alone or in combination with other anticancer agents. These azatyrosine derivatives may be formulated into suitable pharmaceutical dosage forms for the treatment of cancer.

17 Claims, No Drawings

N-BENZOYL-α-ALKYLATED AZATYROSINES AS ANTICANCER AGENTS

FIELD OF INVENTION

This invention relates to the syntheses of a series of N-benzoyl-α-alkylated azatyrosines as novel derivatives of L-azatyrosine, and methods of using the same to treat cancer.

BACKGROUND OF THE INVENTION

Mutated ras genes have been frequently found in human cancers. For example, these mutated ras genes are found in 90% patients of adenocarcinomas of the pancreas, in 50% of the colon cancer patients, and in 50% of the thyroid tumor patients. The high incidence of mutated ras genes in cancer patients has led many investigators to put their research efforts toward treating mutated ras genes and finding the potential anticancer drugs.

The antibiotic L-azatyrosine, first isolated from *Streptomyces chibanesis*, has recently been found to possess important antitumor properties (Inouye, S. etc., *Chem. Pharm. Bull.*, 1975, 23, 2669–77) (Monden, Y. etc., *Gan to Kagaku Ryoho*, 1997, 24, 1563–70). For instance, Shindo-Okada and coworkers reported that L-azatyrosine induces permanent reversion of activated c-Ha-ras-transformed NIH3T3 cells to the apparently normal phenotype, without significantly affecting the growth of cells possessing normal ras gene (Shjindo-Okada, N., etc., Mol. Carcinog., 1989, 2, 159–167) (Krzyzosiak, W. J., etc., *Proc. Natl. Acad. Sci.*, USA, 1992, 89, 4879–83). Studies also proved that L-azatyrosine is involved in the regulation of other oncogenic cell growth. In addition, L-azatyrosine also inhibits 7,12-dimethylbenz[a] anthracene or methylnitrosourea-induced carcinogenesis in mice harboring a normal c-Ha-ras gene (Izawa, M. etc., *Cancer Res.* 1992, 52, 1628–30). In the same reference, Izawa etc. also demonstrated that L-azatyrosine can block pappilomas induced by a chemical carcinogen at a dose of 2 mg/mouse once every two days for 12 days. Recently, L-azatyrosine was shown to inhibit prostate tumorigenic growth. Incubation with azatyrosine (for 7 days) resulted in greater than 95% in-vitro growth inhibition of three parental prostate cancer cell lines (TSU-Prl, DU-145, and PC-3) (Benoit, R. M. etc., *Urology*, 1995, 46, 370–377). It also has high reversion efficiency on human prostate cancer cells. These examples have shown that L-azatyrosine plays a potentially significant therapeutic role in the treatment of the advanced prostate cancer.

One drawback of azatyrosine in potential cancer treatment is its low potency. Relatively high concentrations (1–2 mM) are required for the anticancer activity gene (Shjindo-Okada, N., etc., Mol. Carcinog., 1989, 2, 159–167) (Benoit, R. M. etc., *Urology*, 1995, 46, 370–377). It has been believed that the low rate of transmembrane mechanism by which azatyrosine enters the cell results in the limited efficiency of the compound.

In this invention, a series of N-benzoyl-α-alkylated azatyrosines as novel derivatives of L-azatyrosine was rationally designed to improve the potency of L-azatyrosine.

BRIEF SUMMARY OF THE INVENTION

This invention discloses a series of N-benzoyl-α-alkylated azatyrosine compounds and methods and compositions for using these compounds in the treatment of cancer. These compounds are more effective than L-azatyrosine. These compounds may be used to treat cancer, decrease the growth of a cancer cell, prevent metastases or otherwise be effective against a hyperproliferative disorder such as cancer. These compounds will be useful for any disorder currently being treated with L-azatyrosine.

Other objects, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

DETAILED DESCRIPTION OF THE INVENTION

Due to the intriguing azatyrosine and the crucial ability of α-alkylated amino acids to induce and stabilize some limited conformations themselves or when incorporated into small peptides, a series of α-alkylated derivatives of azatyrosine, which might act with cytostatic activities, has been rationally synthesized. More specifically, this invention discloses the synthesis of a series of N-benzoyl-α-alkylated azatyrosines.

The N-benzoyl-α-alkylated azatyrosines in this invention may be represented by the two formulas as follow:

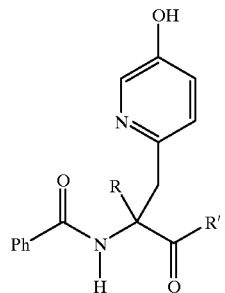

structure I

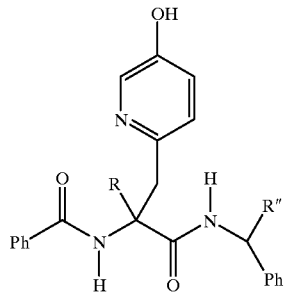

structure II

Where R and R", individually, are lower alkyl and R' is OH, OEt or NH—CH(Ph)—R".

Where "lower alkyl" means a linear, branched, or cyclic hydrocarbon group containing from about 1 to 7 carbons.

The precursor, 7a–c, is synthesized according to Scheme 1 and the procedure may be described as follows:

1. Chemically stable 5-(benzenesulfonyloxy)-2-bromomethylpyridine [4] was prepared from 5-hydroxy-2-methylpyridine [3] in moderate yield (52%) under AIBN (2,2'-azobisisobutyronitrile) and NBS (N-bromosuccinimide) conditions.

2. Hydration of N-benzoylated amino acids [5a–c] in the presence of DCC (dicyclohexylcarbodiimide) afforded 4-monosubstituted 2-phenyloxazol-5(4H)-ones [6a–c].

3. Addition of solid NaH dispersion (60% in mineral oil) under an inert gas to the solution of [6a–c] and [4] in DMF (N'N-dimethylformamide) at 0° and subsequent stirring at room temperature yielded the desired 4'4-disubstituted 2-phenyloxazol-5(4H)-ones [7a–c] in 28–46% yeilds.

These N-benzoyl-α-alkylated azatyrosines are synthesized according to the general procedures shown in Scheme 2. Syntheses of some of these derivatives (such as 8a–c, 9a–c, and 10a–c) are shown in Schemes 2A, 2B, and 2C respectively. The specific of these schemes are given in examples 1–6 are presented herein below.

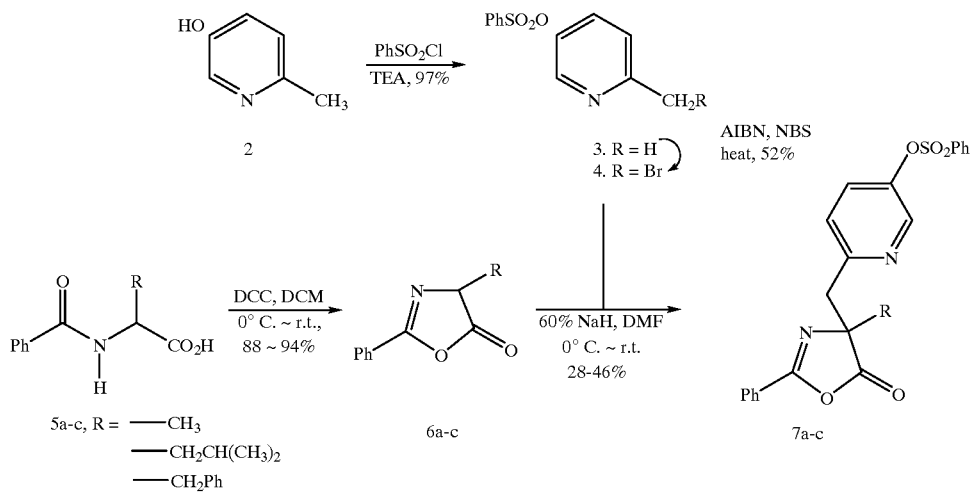

(1) Synthesis of α-alkylated Derivatives of Azatyrosine

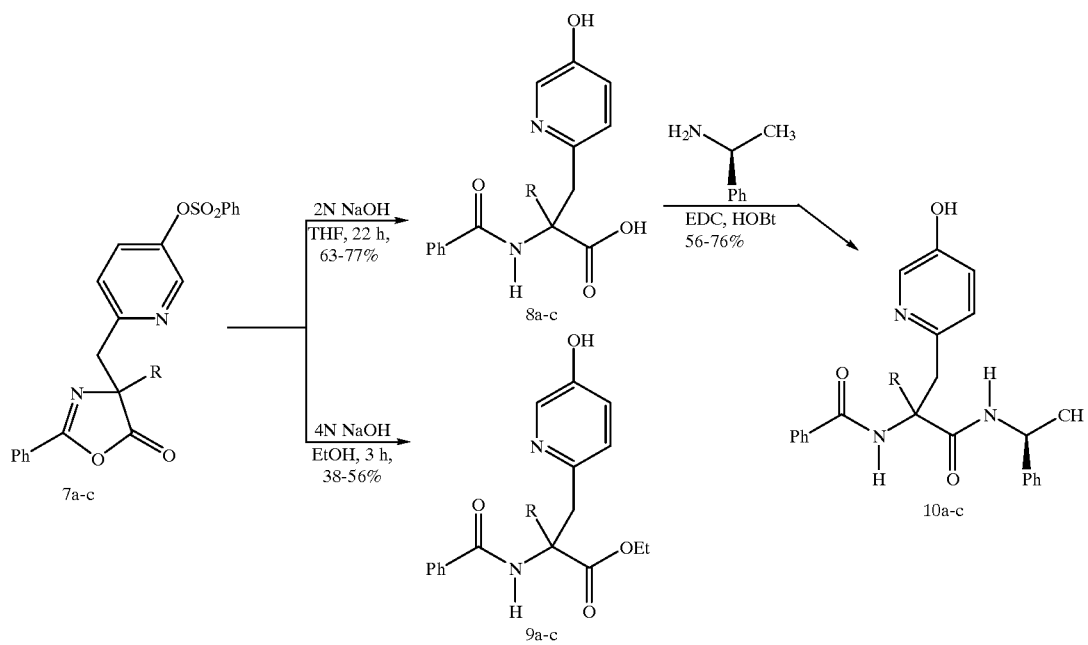

Scheme 2A.
Synthesis of N-Benzoyl-α-alkyl-azatyrosines 8a-c

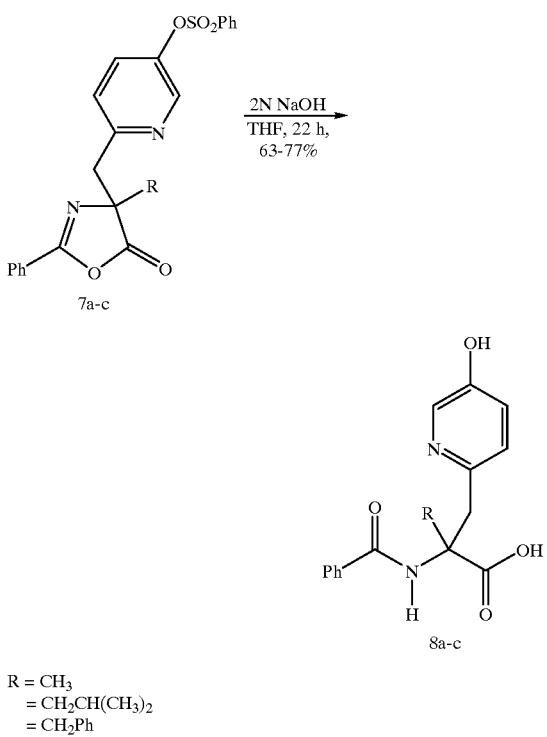

R = CH₃
  = CH₂CH(CH₃)₂
  = CH₂Ph

Scheme 2B.
Synthesis of N-Benzoyl-α-alkyl-azatyrosinates 9a-c

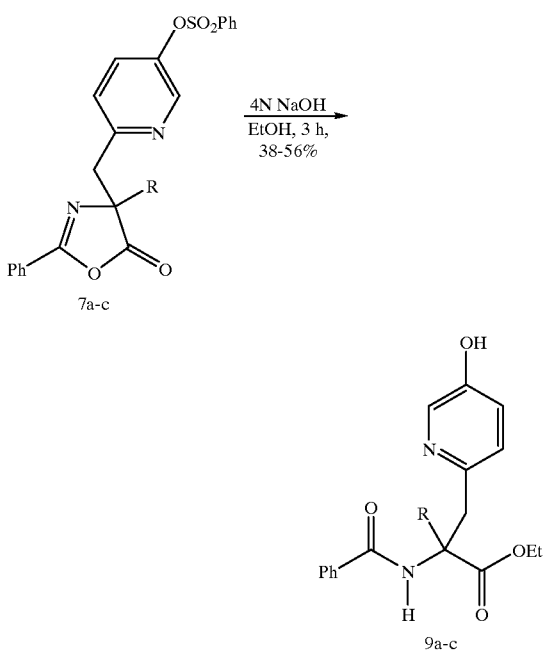

R = CH₃
  = CH₂CH(CH₃)₂
  = CH₂Ph

Scheme 2c.
Synthesis of N-Benzoyl-α-alkyl-azatyrosylamide 10a-c

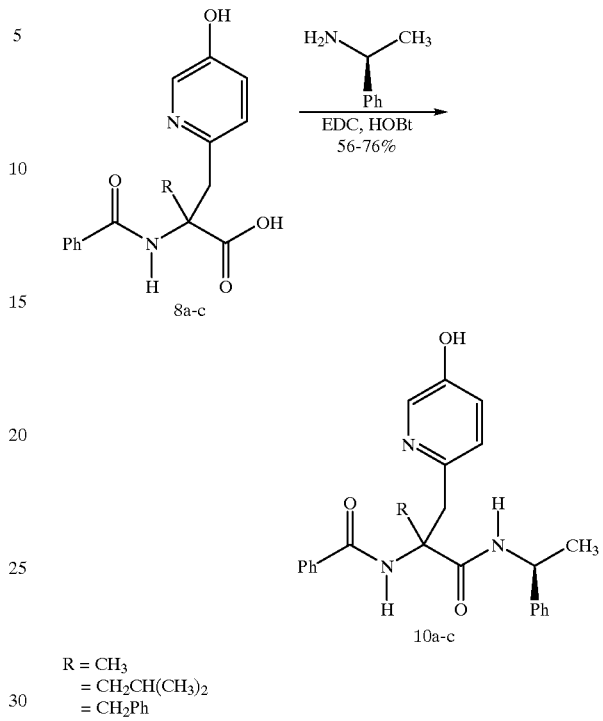

R = CH₃
  = CH₂CH(CH₃)₂
  = CH₂Ph

Pharmaceuticals And Methods Of Treating Cancer

In a particular aspect, the present invention provides methods for the treatment of various malignancies. Treatment methods will involve treating an individual with an effective amount of the N-benzoyl-α-alkylated azatyrosine compounds in this invention, as described herein throughout. An effective amount is described, generally, as that amount sufficient to detectably and repeatedly to ameliorate, reduce, minimize or limit the extent of a disease or its symptoms. More rigorous definitions may apply, including elimination, eradication or cure of disease.

To kill cells, inhibit cell growth, inhibit metastasis, decrease tumor size and otherwise reverse or reduce the malignant phenotype of tumor cells, using the methods and compositions of the present invention, one would generally contact a "target" cell with the N-benzoyl-α-alkylated azatyrosine compounds in this invention. This may be combined with compositions comprising other agents effective in the treatment of cancer. These compositions would be provided in a combined amount effective to kill or inhibit proliferation of the cell. This process may involve contacting the cells with the N-benzoyl-α-alkylated azatyrosine compounds in this invention and the agent(s) or factor(s) at the same time. This may be achieved by contacting the cell with a single composition or pharmacological formulation that includes both agents, or by contacting the cell with two distinct compositions or formulations, at the same time, wherein one composition includes the N-benzoyl-α-alkylated azatyrosine compounds in this invention and the other includes the second agent.

Alternatively, the therapy with the N-benzoyl-α-alkylated azatyrosine compounds in this invention may precede or follow the other agent treatment by intervals ranging from minutes to weeks. In embodiments where the other agent and the N-benzoyl-α-alkylated azatyrosine compounds of this invention are applied separately to the cell, one would generally ensure that a significant period of time did not expire between the time of each delivery, such that the agent and the N-benzoyl-α-aklylated azatyrosine compounds of this invention would still be able to exert an advantageously combined effect on the cell. In such instances, it is contemplated that one would contact the cell with both modalities within about 12–24 h of each other and, more preferably, within about 6–12 h of each other, with a delay time of only about 12 h being most preferred. In some situations, it may be desirable to extend the time period for treatment significantly, however, where several d (2, 3, 4, 5, 6 or 7) to several wk (1, 2, 3, 4, 5, 6, 7 or 8) lapse between the respective administrations.

Administration of the therapeutic the N-benzoyl-α-alkylated azatyrosine compounds of the present invention to a patient will follow general protocols for the administration of chemotherapeutics, taking into account the toxicity, if any, of the N-benzoyl-α-aklylated azatyrosine compounds of this invention. It is expected that the treatment cycles would be repeated as necessary. It also is contemplated that various standard therapies, as well as surgical intervention, may be applied in combination with the described gene therapy.

Where clinical application of a particular therapy is contemplated, it will be necessary to prepare the complex as a pharmaceutical composition appropriate for the intended application. Generally this will entail preparing a pharmaceutical composition that is essentially free of pyrogens, as well as any other impurities that could be harmful to humans or animals. One also will generally desire to employ appropriate salts and buffers to render the complex stable and allow for complex uptake by target cells.

Aqueous compositions of the present invention comprise an effective amount of the compound, dissolved or dispersed in a pharmaceutically acceptable carrier or aqueous medium. Such compositions can also be referred to as inocula. The phrases "pharmaceutically or pharmacologically acceptable" refer to molecular entities and compositions that do not produce an adverse, allergic or other untoward reaction when administered to an animal, or a human, as appropriate. As used herein, "pharmaceutically acceptable carrier" includes any and all solvents, dispersion media, coatings, antibacterial and antifungal agents, isotonic and absorption delaying agents and the like. The use of such media and agents for pharmaceutical active substances is well known in the art. Except insofar as any conventional media or agent is incompatible with the active ingredient, its use in the therapeutic compositions is contemplated. Supplementary active ingredients also can be incorporated into the compositions.

The compositions of the present invention may include classic pharmaceutical preparations. Dispersions also can be prepared in glycerol, liquid polyethylene glycols, and mixtures thereof and in oils. Under ordinary conditions of storage and use, these preparations contain a preservative to prevent the growth of microorganisms.

Depending on the particular cancer to be treated, administration of therapeutic compositions according to the present invention will be via any common route so long as the target tissue is available via that route. This includes oral, nasal, buccal, rectal, vaginal or topical. Topical administration would be particularly advantageous for treatment of skin cancers. Alternatively, administration will be by orthotopic, intradermal, subcutaneous, intramuscular, intraperitoneal or intravenous injection. Such compositions would normally be administered as pharmaceutically acceptable compositions that include physiologically acceptable carriers, buffers or other excipients.

The treatments may include various "unit doses." Unit dose is defined as containing a predetermined-quantity of the therapeutic composition calculated to produce the desired responses in association with its administration, i.e., the appropriate route and treatment regimen. The quantity to be administered, and the particular route and formulation, are within the skill of those in the clinical arts. Also of import is the subject to be treated, in particular, the state of the subject and the protection desired. A unit dose need not be administered as a single injection but may comprise continuous infusion over a set period of time.

Preferably, patients will have adequate bone marrow function (defined as a peripheral absolute granulocyte count of >2,000/mm$^3$ and a platelet count of 100,000/mm$^3$), adequate liver function (bilirubin <1.5 mg/dl) and adequate renal function (creatinine <1.5 mg/dl).

i) Cancer Therapy

One of the preferred embodiments of the present invention involves the use of the N-benzoyl-α-alkylated azatyrosine compounds of this invention to treat cancer cells. Target cancer cells include cancers of the lung, brain, prostate, kidney, liver, ovary, endometrium, breast, skin, stomach, esophagus, head and neck, testicles, germ cancer, epithelial, colon, small intestine, thyroid, cervix, pancreas, glioblastoma, astrocytoma, oligodendroglioma, ependymomas, neurofibrosarcoma, meningia, lymphatic system and blood. Of particular interest are non-small cell lung carcinomas including squamous cell carcinomas, adenocarcinomas and large cell undifferentiated carcinomas.

According to the present invention, one may treat the cancer by directly injection a tumor with the therapeutic compositions of the present invention. Alternatively, the tumor may be infused or perfused with the therapeutic composition using any suitable delivery vehicle. Local or regional administration, with respect to the tumor, also is contemplated. Finally, systemic administration may be performed. In certain embodiments, the contacting comprises delivering the expression construct endoscopically, intratracheally, intralesionally, percutaneously, intravenously, subcutaneously or intratumorally to said subject.

Continuous administration also may be applied where appropriate, for example, where a tumor is excised and the tumor bed is treated to eliminate residual, microscopic disease. Delivery via syringe or catherization is contemplated. Such continuous perfusion may take place for a period from about 1–2 hours, to about 2–6 hours, to about 6–12 hours, to about 12–24 hours, to about 1–2 days, to about 1–2 wk or longer following the initiation of treatment. Generally, the dose of the therapeutic composition via continuous perfusion will be equivalent to that given by a single or multiple injections, adjusted over a period of time during which the perfusion occurs.

For tumors of >4 cm, the volume to be administered will be about 4–10 ml (preferably 10 ml), while for tumors of <4 cm, a volume of about 1–3 ml will be used (preferably 3 ml). Multiple injections delivered as single dose comprise about 0.1 to about 0.5 ml volumes. The viral particles may advantageously be contacted by administering multiple injections to the tumor, spaced at approximately 1 cm intervals.

In certain embodiments, the tumor being treated may not, at least initially, be resectable. Treatments with therapeutic viral constructs may increase the resectability of the tumor due to shrinkage at the margins or by elimination of certain particularly invasive portions. Following treatments, resection may be possible. Additional treatments subsequent to resection will serve to eliminate microscopic residual disease at the tumor site. In certain embodiments, tumor resection may occur prior to the contacting. The tumor resection may be performed one, two, three or more times.

A typical course of treatment, for a primary tumor or a post-excision tumor bed, will involve multiple doses. Typical primary tumor treatment involves a 6 dose application over a two-week period. The two-week regimen may be repeated one, two, three, four, five, six or more times. During a course of treatment, the need to complete the planned dosings may be re-evaluated.

Cancer therapies also include a variety of combination therapies with both chemical and radiation based treatments. Combination chemotherapies include, for example, cisplatin (CDDP), carboplatin and other related platinum anticancer drugs, procarbazine, mechlorethamine, cyclophosphamnide, camptothecin, ifosfamide, melphalan, chlorambucil, bisulfan, nitrosurea, dactinomycin, daunorubicin, doxorubicin, bleomycin, plicomycin, mitomycin, etoposide (VP16), tamoxifen, taxol, transplatinum, 5-fluorouracil, vincristin, vinblastin and methotrexate or any analog or derivative variant thereof.

Other factors that cause DNA damage and have been used extensively include what are commonly known as γ-rays, X-rays, and/or the directed delivery of radioisotopes to tumor cells. Other forms of DNA damaging factors are also contemplated such as microwaves and UV-irradiation. It is most likely that all of these factors effect a broad range of damage on DNA, on the precursors of DNA, on the replication and repair of DNA, and on the assembly and maintenance of chromosomes. Dosage ranges for X-rays range from daily doses of 50 to 200 roentgens for prolonged periods of time (3 to 4 wk), to single doses of 2000 to 6000 roentgens. Dosage ranges for radioisotopes vary widely, and depend on the half-life of the isotope, the strength and type of radiation emitted, and the uptake by the neoplastic cells.

In addition, gene therapy become increasingly useful for treating cancers. In such embodiments, expression constructs comprising viral vectors containing the therapeutic genes are used to in order to induce an apoptotic effect in cancer cells. The viral vectors may be adenoviral (see for example, U.S. Pat. Nos. 5,824,544; 5,707,618; 5,693,509; 5,670,488; 5,585,362; each incorporated herein by reference), retroviral (see for example, U.S. Pat. Nos. 5,888,502; 5,830,725; 5,770,414; 5,686,278; 4,861,719 each incorporated herein by reference), an adeno-associated viral (see for example, U.S. Pat. Nos. 5,474,935; 5,139,941; 5,622,856; 5,658,776; 5,773,289; 5,789,390; 5,834,441; 5,863,541; 5,851,521; 5,252,479 each incorporated herein by reference), an adenoviral-adenoassociated viral hybrid (see for example, U.S. Pat. No. 5,856,152 incorporated herein by reference) a vaccinia viral or a herpesviral (see for example, U.S. Pat. Nos. 5,879,934; 5,849,571; 5,830,727; 5,661,033; 5,328,688 each incorporated herein by reference) vector. These vectors are contacted with the cancer cell to produce the therapeutic effect. The viral expression construct comprising a nucleic acid encoding a therapeutic anticancer gene may any cancer therapy gene known to those of skill in the art including but not limited to p53, p16, p21, MMAC1, p73, zac1, C-CAM, BRCAI, Rb, Bax, Bak, Bim, Bik, Bid, Bad gene, Harakiri, Ad E1B, an ICE-CED3 protease, a cytokine such as IL-2, IL-2, IL-3, IL-4, IL-5, IL-6, IL-7, IL-8, IL-9, IL-10, IL-11, IL-12, IL-13, IL-14, IL-15, TNF, GMCSF, β-interferon and γ-interferon. In other embodiments, the therapeutic nucleic acid may be an antisense nucleic acid directed against an oncogene.

It is understood that the expression vectors comprising the therapeutic genes to be used in combination with the compositions of the present invention, will further comprise the appropriate promoters, enhancers and other regulator elements necessary for efficient replication to occur. Such elements are well known to those of skill in the art. Exemplary promoters for use herein include but are not limited to CMV IE, SV40 IE, RSV, β-actin, tetracycline regulatable and ecdysone regulatable. By "treatment," the present invention refers to any event that decreases the growth, kills or otherwise abrogates the presence of cancer cells in a subject. Such a treatment may also occur by inhibition of the metastatic potential or inhibition of tumorigenicity of the cell so as to achieve a therapeutic outcome.

Various combinations may be employed, the N-benzoyl-α-alkylated azatyrosine compounds in this invention is "A" and the gene, radio- or chemotherapeutic agent is "B":

| | | | | | | |
|---|---|---|---|---|---|---|
| A/B/A | B/A/B | B/B/A | A/A/B | A/B/B | B/A/A | A/B/B/B | B/A/B/B |
| B/B/B/A | B/B/A/B | A/A/B/B | A/B/A/B | A/B/B/A | B/B/A/A | |
| B/A/B/A | B/A/A/B | A/A/A/B | B/A/A/A | A/B/A/A | A/A/B/A | |

The terms "contacted" and "exposed," when applied to a cell, are used herein to describe the process by which the N-benzoyl-α-alkylated azatyrosine compounds of this invention and gene therapeutic construct, a chemotherapeutic or radiotherapeutic agent are delivered to a target cell or are placed in direct juxtaposition with the target cell. To achieve cell killing or stasis, both agents are delivered to a cell in a combined amount effective to kill the cell or prevent it from dividing.

The therapeutic compositions of the present invention are advantageously administered in the form of injectable compositions either as liquid solutions or suspensions; solid forms suitable for solution in, or suspension in, liquid prior to injection may also be prepared. These preparations also may be emulsified. A typical composition for such purpose comprises a pharmaceutically acceptable carrier. For instance, the composition may contain 10 mg, 25 mg, 50 mg or up to about 100 mg of human serum albumin per milliliter of phosphate buffered saline. Other pharmaceutically acceptable carriers include aqueous solutions, non-toxic excipients, including salts, preservatives, buffers and the like. Examples of non-aqueous solvents are propylene glycol, polyethylene glycol, vegetable oil and injectable organic esters such as ethyloleate. Aqueous carriers include water, alcoholic/aqueous solutions, saline solutions, parenteral vehicles such as sodium chloride, Ringer's dextrose, etc. Intravenous vehicles include fluid and nutrient replenishers. Preservatives include antimicrobial agents, anti-oxidants, chelating agents and inert gases. The pH and exact concentration of the various components the pharmaceutical composition are adjusted according to well known parameters.

Additional formulations are suitable for oral administration. Oral formulations include such typical excipients as, for example, pharmaceutical grades of mannitol, lactose, starch, magnesium stearate, sodium saccharine, cellulose, magnesium carbonate and the like. The compositions take the form of solutions, suspensions, tablets, pills, capsules, sustained release formulations or powders. When the route is topical, the form may be a cream, ointment, salve or spray.

EXAMPLES

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Synthesis of N-Benzoyl-α-methyl-DL-azatyrosine (8a)

A solution of 4-[(5-Benzenesulfonyloxypyridin-2-yl) methyl]-4-methyl-2-phenyl-oxazol-5(4H)-one (7a, 422 mg, 1 mmol) in tetrahydrofuran (2 mL) was treated with 2N sodium hydroxide solution (2 mL) at 0° C. The reaction mixture was stirred at room temperature for 22 h and evaporated in vacuo. The resulting residue was dissolved in 10 mL of water, neutralized with 2N hydrogen chloride solution to pH 3 and extracted with dichloromethane (2×15 mL). The combined organic layers were dried over anhydrous sodium sulfate and concentrated in vacuo. The resulting residue was purified by silica gel chromatography ($CH_2Cl_2$/MeOH/AcOH (10:1:0.1) as eluents) to furnish 190 mg (63%) of 8a as a pale yellow solid: mp 137–140° C.; $^1$H NMR (300 MHz, $CD_3OD$): 8.06 (d, J=2.2 Hz, 1H), 7.67 (dd, J=1.4, 8.4 Hz, 2H), 7.7.57–7.15 (m, 6H), 3.32 (s, 2H), 1.54 (s, 3H); FABMS (NBA as matrix): m/z 301.2 $[M+H]^+$; HR-FABMS: exact mass calcd for $C_{16}H_{17}N_2O_4$ $(M+H)^+$ 301.1460, found 301.1186.

Example 2

Synthesis of N-Benzoyl-α-isobutyl-DL-azatyrosine (8b)

A solution of 4-[(5-Benzenesulfonyloxypyridin-2-yl) methyl]-4-isobutyl-2-phenyl-oxazol-5(4H) -one (7b, 630 mg, 1.36 mmol) in 3 mL of THF was treated with 3 mL of 2N sodium hydroxide solution at 0° C. The reaction mixture was stirred at room temperature for 22 h and evaporated in vacuo. The resulting residue was dissolved in 10 mL of water, neutralized with 2N hydrogen chloride solution to pH 3 and extracted with dichloromethane (2×15 mL). The combined organic layers were dried over anhydrous sodium sulfate and concentrated in vacuo. The residue was purified by silica gel chromatography ($CH_2Cl_2$/MeOH/AcOH (10:1:0.1) as eluent) to furnish 360 mg (77%) of 8b as a pale yellow solid: mp 245–248° C.; $^1$H NMR (300 MHz, DMSO-$d_6$): 7.94 (s $_{br}$, 1H), 7.82–7.78 (m, 1H), 7.64–7.58 (m, 2H), 7.54–7.42 (m, 3H), 7.00–6.84 (m, 2H), 3.40–3.20 (m, 2H $CH_2Py$), 2.25–2.15 (m,1H), 1.88–1.66 (m, 2H), 0.85 (d, J=6.4 Hz, 6H); FABMS (NBA as matrix): m/z 343.1 $[M+H]^+$; HR-FABMS: exact mass calculated for $C_{19}H_{23}N_2O_4(M+H)^+$ 343.1872, found 343.1676.

Example 3

Ethyl N-benzoyl-α-isobutyl-DL-azatyrosinate (9b)

A solution of 4-[(5-Benzenesulfonyloxypyridin-2-yl) methyl]-4-isobutyl-2-phenyl-oxazol-5(4H) -one (7b, 0.40 g, 0.86 mmol) in EtOH (1.2 mL) was treated with 4N NaOH (0.4 mL) at 0° C. The reaction mixture was stirred at room temperature for 3 h and diluted with 5 mL of water. The mixture was extracted with ethyl acetate (3×10 mL) and the combined organic layers were dried over anhyrous sodium sulfate and evaporated in vacuo. The residue was purified by silica gel chromatography (n-hexane/ethyl acetate (2:1→1:2) as eluent) to furnish 120 mg (38%) of 9b as a white solid: mp 149–151° C.; $^1$H NMR (300 MHz, $CDCl_3$): 8.01 (s, 1H, OH), 7.70–7.30 (m, 6H, Ar—H), 7.00–6.80 (m, 2H, Ar—H), 4.30–4.15 (m, 2H, O—$CH_2$), 3.90 (d, J=13.8 Hz, 0.5H), 3.24 (d, J=13.8 Hz, 0.5H); 2.70 ($q_{AB}$, J=5.7, 13.8 Hz, 0.5H), 2.00 ($q_{AB}$, J=7.1, 13.8 Hz, 0.5H), 1.70–1.50 (m, 1H), 1.40–1.20 (m, 2H), 0.91 (d, J=7.1 Hz, 3H), 0.83 (d, J=6.6 Hz, 3H); FABMS (NBA as matrix): m/z 371.1 $[M+H]^+$; HR-FABMS: exact mass calculated for $C_{21}H_{27}N_2O_4(M+H)^+$371.2182, found 371.1991.

Example 4

Ethyl N-benzoyl-α-benzyl-DL-azatyrosinate (9c)

A solution of 4-[(5-Benzenesulfonyloxypyridin-2-yl) methyl]-4-benzyl-2-phenyl-oxazol-5(4H)-one (7c, 0.35 g, 0.7 mmol) in EtOH (1 mL) was treated with 4N NaOH (0.35 mL) at 0° C. The reaction mixture was stirred at room temperature for 3 h and diluted with 5 mL of water. The mixture was extracted with ethyl acetate (3×10 mL) and the combined organic layers were dried over anhydrous sodium sulfate and evaporated in vacuo. The residue was purified by silica gel chromatography (n-hexane/ethyl acetate (2:1→1:2) as eluent) to give 90 mg (32%) of 9c as a white solid: mp 181–183° C.; $^1$H NMR (300 MHz, $CDCl_3$): 8.04 (s, 1H, OH), 7.60–6.90 (m, 13H), 4.22 (q, J=6.9 Hz, 2H, O—$CH_2$), 3.91 (dd, J=5.7, 13.8 Hz, 2H), 3.53, 3.38 (2d, J=13.8 Hz, 2H); FABMS (NBA as matrix): m/z 405.2 $[M+H]^+$; HR-FABMS: exact mass calculated for $C_{24}H_{25}N_2O_4(M+H)^+$405.2085, found 405.1812.

Example 5

N-Benzoyl-α-isobutyl-DL-azatyrosyl-(S)-1-phenylethylamide (10b)

To a solution of N-benzoyl-α-isobutyl-DL-azatyrosine (8b, 180 mg, 0.53 mmol) and (S)-1-phenylethylamine (70 mg, 0.58 mmol) in 4 mL of N,N-dimethylformamide was added 1-(3-dimethylaminopropyl)-3-ethyl-carbodiimide (112 mg, 0.58 mmol), N-hydroxy-benzotriazole (80 mg, 0.58 mmol), and followed by diisopropylethylamine (0.1 mL, 0.58 mmol) at 0° C. and an inert gas. The reaction mixture was stirred at 0° C. for 14 h and quenched with water (5 mL) and ethyl acetate (10 mL). The aqueous layer was extracted with additional ethyl acetate (5 mL). The combined organic layers were washed with 5% aqueous sodium bicarbonate, brine, and dried over anhydrous sodium sulfate and filtered. The solvent was concentrated in vacuo and the residue was purified by silica gel chromatography (n-hexane/ethyl acetate (3:1→1:2) as eluents) to yield 160 mg (72%) of 10b as a pale yellow solid: mp 78–79° C., $^1$H NMR (300 MHz, $CDCl_3$): 8.80 (d, J=7.4 Hz, 1H), 8.16 (d, J=11.4 Hz, 1H), 7.90–7.20 (m, 11H), 7/05–6.90 (m, 2H), 5.05–4.95 (m, 1H), 3.65–3.35 (m, 2H), 2.45–2.35 (m, 1H), 1.70–1.50 (2m, 2H), 0.90–0.60 (m, 6H); FABMS (NBA as matrix): m/z 446.2 $[M+H]^+$; HR-FABMS: exact mass calcd for $C_{26}H_{32}N_3O_3(M+H)^+$446.2616, found 446.2441.

Example 6

N-Benzoyl-α-benzyl-DL-azatyrosyl-(S)-1-phenylethylamide (10c)

To a solution of N-benzoyl-α-benzyl-DL-azatyrosine (8c, 100 mg, 0.27 mmol) and (S)-1-phenylethylamine (35 mg, 0.29 mmol) in 2 mL of N,N-dimethylformamide was added 1-(3-dimethylaminopropyl)-3-ethyl-carbodiimide I (56 mg, 0.29 mmol), N-hydroxy-benzotriazole (40 mg, 0.29 mmol), and followed by diisopropylethylamine (0.08 mL, 0.46 mmol) at 0° C. and an inert gas. The reaction mixture was stirred at 0° C. for 14 h and quenched with water (5 mL) and ethyl acetate (10 mL). The aqueous layer was extracted with additional ethyl acetate (5 mL). The combined organic layers were washed with 5% aqueous sodium bicarbonate, brine, and dried over sodium sulfate and filtered. The solvent was concentrated in vacuo and the residue was purified by silica gel chromatography (n-hexane/ethyl acetate (2:1→1:2) as eluent) to yield 92 mg (76%) of 10c as a pale yellow solid: mp 92–94° C. $^1$H NMR (300 MHz, CDCl$_3$): 9.14, 8.97 (2d, J=7.3 Hz, 1H, NH), 8.84, 8.71 (2s, 1H, OH), 8.10–8.05, 7.85–7.75, 7.55–6.85 (3m, 18H), 5.10–4.90 (m, 1H), 3.70–3.40, 3.30–3.10 (m, 4H), 1.52, 1.41 (2d, J=6.9 Hz, 3H); FABMS (NBA as matrix): m/z 480.2 [M+H]$^+$; HR-FABMS: exact mass calculated for C$_{30}$H$_{30}$N$_3$O$_3$(M+H)$^+$480.2463, found 480.2303.

Example 7
In-vitro Biological Activity Studies

In vitro biological studies in human tumor cell lines assay revealed that these α-alkylated azatyrosines showed improved cytotoxicity on both BC-M1 (breast cancer) and SC-M1 (stomach cancer) cell lines compared with L-azatyrosine. The in-vitro studies for evaluating these α-alkylated derivatives of azatyrosine were performed and the general procedures are listed as follow:

Cell Lines and Cell Culture

Human stomach cancer cell line (SC-M1), and human breast cancer cell line (BC-M1) sampled from inpatients at Tri-service General Hospital in Taipei (Taiwan) were cultured and used in the experiments. All cells from primary culture and subculture were grown in 10% RPMI 1640 supplemented with 100 U/mL penicillin G, 100 µg/mL amphotericin B, and 10% fetal calf serum (FCS) in a 5% CO$_2$ incubator at 37° C.

Cytotoxic Assay by Colorimetric MTT Assay

The cytotoxicity of these compounds against cultured cancer cells was determined by utilizing in-vitro MTT assay. L-azatyrosine and its α-alkylated derivatives were dissolved in milli-Q water at a concentration of 1 mg/mL and diluted with 10% FCS-RPMI to various concentrations, respectively. Single cell suspension (100 µL) and each compounds (100 µL) were added to 96-well flat-bottom microplate. 10% FCS-RPMI (100 µL) was used as a control group. After 3 days incubation at 37° C. in a 5% CO$_2$ incubator, stock MTT (10 µL of 5 mg/mL for each 100 µL solution in well) solution was added to all wells. After additional 2 h incubation in a 5% CO$_2$ incubator, The mixture was centrifuged (1000 rpm for 5 min) and the supernatant was carefully pipetted out. The residue was mixed well with DMSO (100 µL). The optical density of plates was recorded on a MRX Spectrophotometer (Dynatech, Guernsey, UK) at a wavelength of 550 nm.

Data Analysis for Cytotoxicity

Fractional inhibition was calculated as [1-(optical density of sample/optical density of control)]. The IC$_{50}$ values for each compound were determined as a parameter for cytotoxicity, which is the concentration of a test compound exerting 50% survival of cancer cells, compared to untreated controls. Each value is the mean of four experiments. A specific example of the in-vitro study is shown Example 8.

Example 8
in-vitro Biological Activity Studies

A series of α-alkylated derivatives of L-azatyrosine were studied for their in-vitro effects according to the above procedures. The growth inhibition of L-azatyrosine and its derivatives on human cancer cell lines (BC-M1 and SC-M1) has been shown on Table 1.

As shown in Table 1, IC$_{50}$s of these compounds were significantly lower than that of L-azatyrosine as expected. With bigger group attached to amide chain, 10b and 10c exhibit higher growth inhibition than that of L-azatyrosine. Most significantly, compound 10c showed an excellent cytotoxicity on SC-M1 compared with L-azatyrosine (IC$_{50}$s 0.08 mM vs 1.6 mM).

TABLE 1

Growth inhibition of L-azatyrosine and its α-alkylated derivatives on breast cancer cell (BC-M1) and stomach cancer cell (SC-M1) lines[a]

| Compound | R | R' | IC$_{50}$ (mM)[b] BC-M1 | SC-M1 |
|---|---|---|---|---|
| L-Azatyrosine | — | — | 2.2 | 1.6 |
| 8a | methyl | OH | 1.3 | 0.8 |
| 8b | isobutyl | OH | 1.0 | 1.2 |
| 8c | benzyl | OH | 0.6 | 0.6 |
| 9b | isobutyl | OEt | 0.7 | 0.6 |
| 9c | benzyl | OEt | 0.9 | 1.0 |
| 10b | isobutyl | —(S)—NHCH(Ph)CH$_3$ | 0.3 | 0.3 |
| 10c | benzyl | —(S)—NHCH(Ph)CH$_3$ | 0.6 | 0.08 |

[a]10000 cells per well
[b]data presented as mean of 4 experiments

Example 9
Pharmaceutical Dosage Forms Made From N-benzoyl-α-alkylated Azatyrosines The N-benzoyl-α-alkylated azatyrosines in this invention may be formulated with customary pharmaceutical excipients to make suitable dosage forms by standard pharmaceutical technique and process. Said dosage form may be used to treat cancer by oral or parenteral administration. More specifically, said dosage form may be used to treat prostate cancer.

The N-benzoyl-α-alkylated azatyrosines in this invention may be formulated with customary pharmaceutical excipients to make suitable dosage forms by standard pharmaceutical technique and process. Said pharmaceutical excipients include, but not limited to, starch, cellulose, lactose, magnesium stearate, talc, calcium phosphate, surfactant, silicon dioxide, and food color. An example of the dosage form is as follows:

Example 10
A Pharmaceutical Dosage Form Made From Compound 10c

1. Weigh 50 mg of compound 10c; mix well with 50 mg of lactose to form part I.
2. Weigh 60 mg of microcrystalline cellulose; mix with 30 mg of lactose to form part II.
3. Add part I into part II; mix well; add 5 mg of magnesium stearate and mix for three minutes to form part III.

Compress part III by standard tablet press into suitable tablets.

These N-Benzoyl-α-alkyl-azatyrosines in this invention are believed to be new. Based on the in-vitro and mice studies data from the references and the studies from this invention, these L-azatyrosine derivatives may be concluded to be effective in treating cancer. Suitable pharmaceutical dosage forms may be made by standard pharmaceutical technique. They may be used to treat cancer, either alone or in combination with other anticancer chemotherapeutic agents, including, but not limited to, cisplatin, carboplatin, and other platinum drugs.

Ramification and Scope

In conclusion, this invention comprises a series of N-benzoyl-α-alkylated azatyrosines, the preparation, and the use of said compounds for the treatment of cancer.

Although the description above contains many specificities, these should not be construed as limiting the scope of the invention but as merely providing the illustrations of some of the presently preferred embodiments of this invention.

Thus, the scope of this invention should be determined by the appended claims and their legal equivalents, rather than by the examples given.

I claim:

1. An N-benzoyl-α-alkylated azatyrosine compound having a formula as shown in the following structures I or II:

structure I

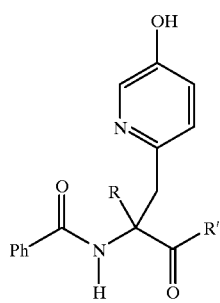

structure II

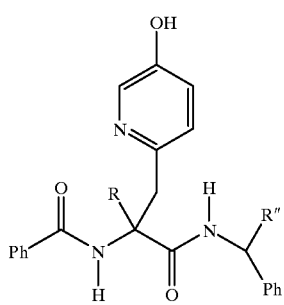

where R and R″, individually, are lower alkyl; R′ is —OH, —OC$_2$H$_5$, or —NHCH(Ph)R″, wherein "lower alkyl" means a linear, branched, or cyclic hydrocarbon group containing from about 1 to 7 carbons.

2. A method of inhibiting the growth of a cancer cell which comprising contacting said cancer cell with an effective amount of a compound having the formula set forth in structure I or structure II:

structure I

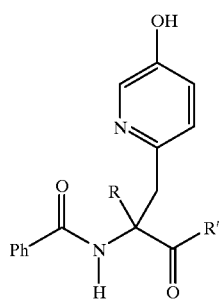

structure II

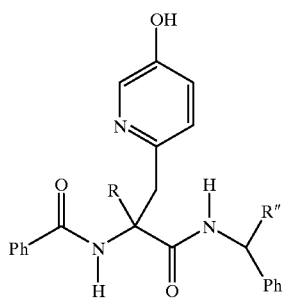

where R and R″, individually, are lower alkyl; R′ is —OH, —OC$_2$H$_5$, or —NHCH(Ph)R″, wherein "lower alkyl" means a linear, branched, or cyclic hydrocarbon group containing from about 1 to 7 carbons.

3. The method in claim 2 where cancer cell is a breast cancer cell, stomach cancer cell, or prostate cancer cell.

4. A pharmaceutical composition comprising:

(i) a compound having the formula set forth in structure I or structure II:

structure I

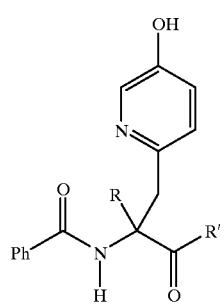

structure II

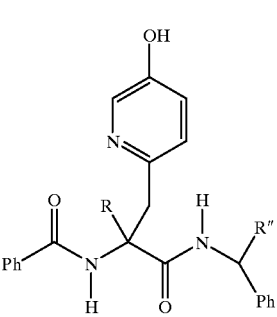

where R and R″, individually, are lower alkyl; R′ is —OH, —OC$_2$H$_5$, or —NHCH(Ph)R″, wherein "lower alkyl" means a linear, branched, or cyclic hydrocarbon group containing from about 1 to 7 carbons; and (ii) a pharmaceutically acceptable buffer, solvent or diluent.

5. A method of treating cancer comprising administering to a cancer patient a therapeutically effective amount of a pharmaceutical composition comprising:

(i) a compound having the formula set forth in structure I or structure II:

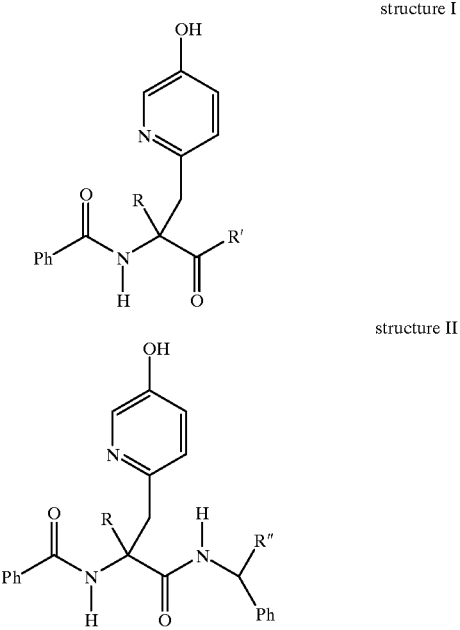

where R and R", individually, are lower alkyl; R' is —OH, —OC$_2$H$_5$, or —NHCH(Ph)R", wherein "lower alkyl" means a linear, branched, or cyclic hydrocarbon group containing from about 1 to 7 carbons; and (ii) a pharmaceutically acceptable buffer, solvent or diluent.

6. The method in claim 5 where cancer is breast cancer, stomach cancer, or prostate cancer.

7. The method of claim 5 wherein said pharmaceutically acceptable form is administered once every one to four weeks.

8. The method of claim 7 wherein said regimen is repeated until remission of said cancer is observed.

9. The method of claim 5 wherein said administration is oral or parenteral.

10. The method of claim 5, further comprising contacting said cancer patient with an additional cancer therapeutic agent.

11. The method of claim 10, wherein said cancer therapeutic agent is selected from the group consisting of tumor irradiation, and a chemotherapeutic agent.

12. The method of claim 11, wherein said chemotherapeutic agent is a DNA damaging agent selected from the group consisting of verapamil, podophyllotoxin, carboplatin, procarbazine, mechlorethamine, cyclophosphamide, camptothecin, ifosfamide, melphalan, chlorambucil, bisulfan, nitrosurea, dactinomycin, daunorubicin, doxorubicin, bleomycin, plicomycin, mitomycin, etoposide (VP16), tamoxifen, taxol, transplatinum, 5-fluorouracil, vincristin, vinblastin and methotrexate.

13. The method of claim 11, wherein said radiation is selected from the group consisting of X-ray radiation, UV-radiation, γ-radiation, or microwave radiation.

14. The method of claim 5, wherein said administering is effected by local delivery of said pharmaceutical composition. percutaneously, intravenously, subcutaneously or intratumorally.

15. The method of claim 5, wherein said administering is effected by direct injection of a tumor in said cancer patient with said pharmaceutical composition.

16. The method of claim 5, wherein said administering comprises delivering said pharmaceutical composition endoscopically, intratracheally, intralesionally, percutaneously, intravenously, subcutaneously or intratumorally.

17. The method of claim 5, further comprising the step, prior to said administering, of resection of a tumor in said cancer patient.

* * * * *

UNITED STATES PATENT AND TRADEMARK OFFICE
CERTIFICATE OF CORRECTION

PATENT NO. : 6,037,357 Page 1 of 1
APPLICATION NO. : 09/296445
DATED : March 14, 2000
INVENTOR(S) : Ming-Kuan Hu It is certified that error appears in the above-identified patent and that said Letters Patent is hereby corrected as shown below:

<u>In the Claims</u>

In claim 14, lines 3-4, delete "percutaneously, intravenously, subcutaneously or intra-tumorally." .

Signed and Sealed this

Seventeenth Day of July, 2007

JON W. DUDAS
*Director of the United States Patent and Trademark Office*